United States Patent
Kulkarni et al.

(10) Patent No.: US 9,247,869 B2
(45) Date of Patent: Feb. 2, 2016

(54) COMPACT FOLDABLE APPARATUS FOR OPHTHALMOLOGY

(71) Applicants: Manish Dinkarrao Kulkarni, Pleasanton, CA (US); Manmohan Singh Sidhu, Porterville, CA (US)

(72) Inventors: Manish Dinkarrao Kulkarni, Pleasanton, CA (US); Manmohan Singh Sidhu, Porterville, CA (US)

(73) Assignee: NETRA SYSTEMS, INC, Pleasanton, CA (US)

( * ) Notice: Subject to any disclaimer, the term of this patent is extended or adjusted under 35 U.S.C. 154(b) by 0 days.

(21) Appl. No.: 13/744,415

(22) Filed: Jan. 18, 2013

(65) Prior Publication Data

US 2014/0204337 A1    Jul. 24, 2014

Related U.S. Application Data

(60) Provisional application No. 61/587,132, filed on Jan. 17, 2012.

(51) Int. Cl.
| | | |
|---|---|---|
| *A61B 3/14* | (2006.01) | |
| *A61B 3/10* | (2006.01) | |
| *A61B 3/00* | (2006.01) | |

(52) U.S. Cl.
CPC ............... *A61B 3/0083* (2013.01); *A61B 3/102* (2013.01)

(58) Field of Classification Search
USPC .................................................. 351/200–246
See application file for complete search history.

(56) References Cited

U.S. PATENT DOCUMENTS

| | | | | |
|---|---|---|---|---|
| 6,106,123 | A * | 8/2000 | McDonald .................... 359/872 |
| 6,616,278 | B2 * | 9/2003 | Gohno et al. ................. 351/245 |
| 7,331,669 | B2 * | 2/2008 | Elsner ........................... 351/206 |
| 7,594,728 | B2 * | 9/2009 | Seal et al. ..................... 351/210 |
| 2013/0286353 | A1 * | 10/2013 | Steinmetz et al. ............ 351/245 |

\* cited by examiner

*Primary Examiner* — Mohammed Hasan

(57) ABSTRACT

There is a need for robust and portable system, and apparatus for ophthalmology. We propose use of folding apparatus for ocular purposes for the first time. Our system will have a chin-rest (or face-rest or forehead rest) that can be folded so that the ocular device could be transported in a brief-case type casing.

20 Claims, 3 Drawing Sheets

COMPACT FOLDABLE APPARATUS FOR OPHTHALMOLOGY

CROSS REFERENCE TO RELATED APPLICATIONS

The instant application claims priority to provisional U.S. patent application 61/587,132 titled "A Compact Foldable Apparatus for Ophthalmology", filed on 17 Jan. 2012 by the inventors Manmohan Singh Sidhu and Manish D. Kulkarni. This benefit is claimed under 35. U.S.C. $119 and the entire disclosure of the Provisional U.S. patent Application No. 61/587,132 is incorporated here by reference.

FIELD OF TECHNOLOGY

The following description relates to a system, and an apparatus for ophthalmology. The device can be used for diagnosis, evaluation or therapy. The device can be used for ophthalmic imaging and/or diagnosis, anterior segment imaging and/or diagnosis, retinal imaging and/or diagnosis. The apparatus can be used for the eyes of humans as well as animals.

BACKGROUND

Most of the ophthalmic systems comprise of the chin-rests that are not foldable. A patient, (whose eye needs to be examined), rests his/her chin on this chin-rest so that the eye can be stabilized for useful measurements on the eye. While useful for stabilizing the patient's eye, these chin-rests form a significant part of the device's footprint. Such a chin-rest is a significant hurdle for minimizing the device-form-factor, and building an apparatus that is compact and portable. European patent (publication number EP1441640 A2 and EP1441640A4, filed Oct. 16, 2002 by E. Ann Elsner) discusses a foldable head or chin-rest. However it does so very briefly without providing design details and only in the context of digital imaging of the retina and anterior segment. It does not discuss optical coherence tomography/optical coherence domain reflectometry (OCDR). Proposed design is more detail, generic and all inclusive of various ophthalmic modalities.

SUMMARY

The invention discloses a foldable system, and a foldable apparatus for ophthalmology. The apparatus can be used for diagnosis, evaluation or therapy. The device can be used for ophthalmic imaging and/or diagnosis, anterior segment imaging and/or diagnosis, retinal imaging and/or diagnosis. The apparatus can be used for the eyes of humans as well as animals. In the proposed system, the chin-rest can be folded to save the space when the device is not in operation. This saves space while the device is in storage or under transportation.

In one embodiment, the apparatus comprises of an ophthalmic system comprising of at least one means to hold the face of a patient (i.e., face-holder), a diagnostic component to perform diagnosis or evaluation of the eye or a therapeutic component for the treatment of the eye and the means to fold the face-holder. Such a device can be termed as a "foldable face-holder apparatus".

In another embodiment, the face-holder can be folded at least once and possibly multiple times.

In another embodiment the face-holder comprises of a resting pad to rest forehead (i.e., forehead rest).

In another embodiment, the face-holder comprises of a resting pad to rest the chin (i.e., chin-rest).

In another embodiment, the face-holder can be folded by collapsing multi-stage telescopic legs.

In another embodiment, the face-holder comprises of a chin-rest and a forehead rest and only the portion between the chin-rest and the instrument base is collapsible using multi-stage telescopic legs.

In another embodiment, the face-holder comprises of a chin-rest and a forehead rest and only the portion below the chin-rest and the instrument base is collapsible using multi-stage telescopic legs.

In one more embodiment, there is a folding hinge at or near the chin-rest.

In an embodiment, there is a folding hinge for the face holder at or near the instrument base.

In another embodiment, the proposed ophthalmic system comprises of at least one means to hold the face of a patient (i.e., face-holder) and the means to eject or remove the face-holder from the base of the instrument.

In another embodiment, the chin-rest can be removed or ejected using a button from the base of the instrument.

In another embodiment, the chin-rest is attached to the base of the instrument. In some other embodiments, the chin-rest-attachment is removable.

In another embodiment, the chin-rest is attached to the pole of the face-holder. and the chin-rest can be ejected or removed from the pole of the face-holder.

In one more embodiment, an ophthalmic system comprises of at least one means to hold the face of a patient (i.e., face-holder), an ocular diagnostic or therapeutic component and the means to remove the face-holder from the instrument and attach it to the patient's face.

In another embodiment, the face-holder is attached to the eyes using a head-band. In some embodiments, face-holder comprises of a chin-rest.

In some other embodiments, the face-holder is attached to the eyes using spectacles-type assembly. The eye-piece may be moved from one eye to the other for analyzing both the eyes.

In some embodiments, the apparatus is used for ophthalmic imaging.

In some other embodiments, the apparatus is used for optical coherence tomography (OCT) imaging.

In some other embodiments, the foldable face-holder apparatus comprises of optical coherence tomography (OCT) imaging apparatus and the OCT apparatus comprises of a spectrometer to implement spectral-domain OCT.

In some other embodiments, the foldable face-holder apparatus comprises of optical coherence tomography (OCT) imaging apparatus and the OCT apparatus comprises of a tunable wavelength (or frequency) light source to implement swept-source OCT.

In some other embodiments, the foldable face-holder apparatus comprises of optical coherence tomography (OCT) imaging apparatus and the OCT apparatus comprises of a depth-scanning reference mirror to implement time-domain OCT.

In some other embodiments, the apparatus comprises of means to shift the eye-piece (which is optics used to focus on the eye) towards the left or right eye.

In some embodiments, the eye-piece is shifted using a precision slide.

In some other embodiments, the eye-piece is shifted using a sliding rod.

In some embodiments, the eye-piece is positioned using a micro-precision slide.

In some embodiments, the foldable face-holder apparatus comprises of the means for an eye-fixation target.

In some embodiments, the apparatus comprises of fiber or cables running from the instrument to the eye.

In some embodiments, the apparatus comprises of a screen to display measurement or imaging results.

In some other embodiments the display screen is a touch-sensitive screen.

In some embodiments, the base of the apparatus comprises of electronics and optical components.

In some embodiments, all the apparatus components reside in a brief-case.

In some embodiments, the brief-case has wheels and/or a handle to assist transportation.

In some embodiments, the apparatus operates on batteries. In some other embodiments, these batteries can be rechargeable batteries. The batteries can be charged independently or by connecting a charger to the apparatus. The charger can source power from the electrical wiring in a building or any other power source. The charger can also source power from a vehicle such as a car or a bus or a truck or a van. The charger can also source power from the vehicle's engine.

In some embodiments, the apparatus evaluates or scans the retina and/or the posterior segment. In some other embodiments, the apparatus evaluates or scans the cornea and/or anterior segment.

DETAILED DESCRIPTION

The instant disclosure describes a technological advancement of foldable ophthalmic apparatus and system. Such a system would be compact, portable and would save storage space.

Figure 1:
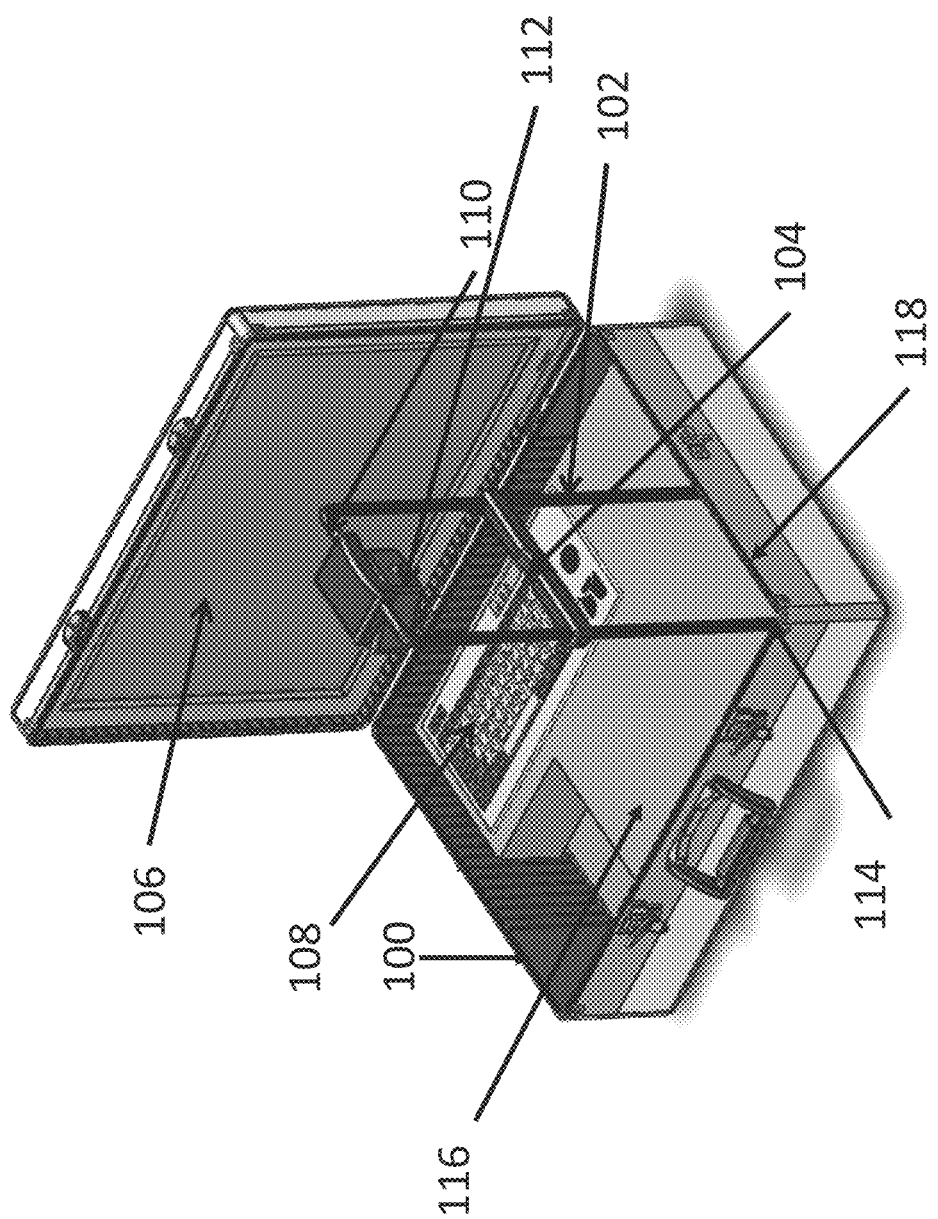
FIG. 1 depicts a simplified version of the "foldable face-holder apparatus" 100.

FIG. 1 depicts a simple version of the "foldable face-holder apparatus" 100. The apparatus comprises of an ophthalmic system comprising of at least one means to hold the face of a patient (i.e., face-holder 102), a diagnostic component to perform diagnosis or evaluation or a therapeutic component to perform treatment of the eye and the means to fold the face-holder (e.g., hinge 114). Thus the apparatus and system will comprise of at least one of diagnostic, evaluation and therapeutic components.

In some embodiments, the face-holder can be folded at least once and possibly multiple times. In some embodiments, the face-holder comprises of a resting pad to rest forehead (i.e., forehead rest 110). In another embodiment, the face-holder comprises of a resting pad to rest chin (i.e., chin-rest 104).

Figure 3:
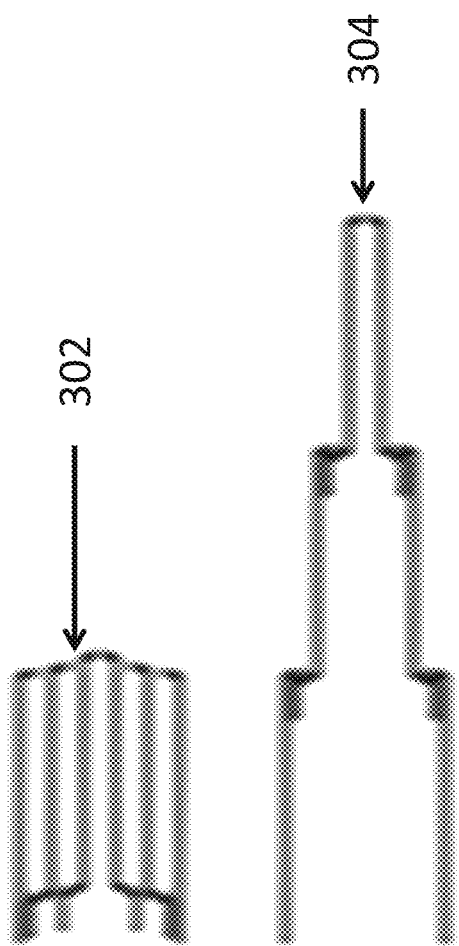
FIG. 3 illustrates telescopic legs.

In another embodiment of the instant apparatus, the face-holder can be folded by collapsing multi-stage telescopic legs. In another embodiment, the face-holder comprises of a chin-rest 104 and a forehead rest 110 and only the portion between the chin-rest 104 and the instrument base 118 is collapsible using multi-stage telescopic legs (FIG. 3).

In some other embodiments, the apparatus comprises of an eye-piece 112 which is optics and mechanics used to evaluate or treat the eye.

In some embodiments, the apparatus comprises of a screen 106 to display measurement or imaging results. Thus, the display can host diagnostic-assisting results. In some other embodiments the display screen 106 is a touch-sensitive screen. In some other embodiments, the display could be 3-D showing 3-dimensional features of the data or the measurements or anatomic features.

In some embodiments, the apparatus comprises of a keyboard 108 to control the apparatus. The keyboard 108 can optionally comprise of a mouse or a controlling ball or a joystick. In some other embodiments the keyboard 108 is a touch-sensitive screen.

In some embodiments, the eye-piece is shifted using a precision slide to evaluate or treat the left or right eye. In some other embodiments, the eye-piece is shifted using a sliding rod. In some embodiments, the eye-piece is positioned using a micro-precision slide.

In some embodiments, the eye-piece has railings to move it forward or backward with respect to the patient's eye.

In some embodiments, the foldable face-holder apparatus comprises of the means for an eye-fixation target. These means could comprise of a display inside the eye-piece 112. The display could have an eye-fixation target as desired by the operator of the apparatus.

In some embodiments, the base 118 of the apparatus comprises of electronics and optical components. In some other embodiments of the invention, the apparatus comprises of fiber or cables running from the base 118 to the eye-piece 112.

Figure 2:
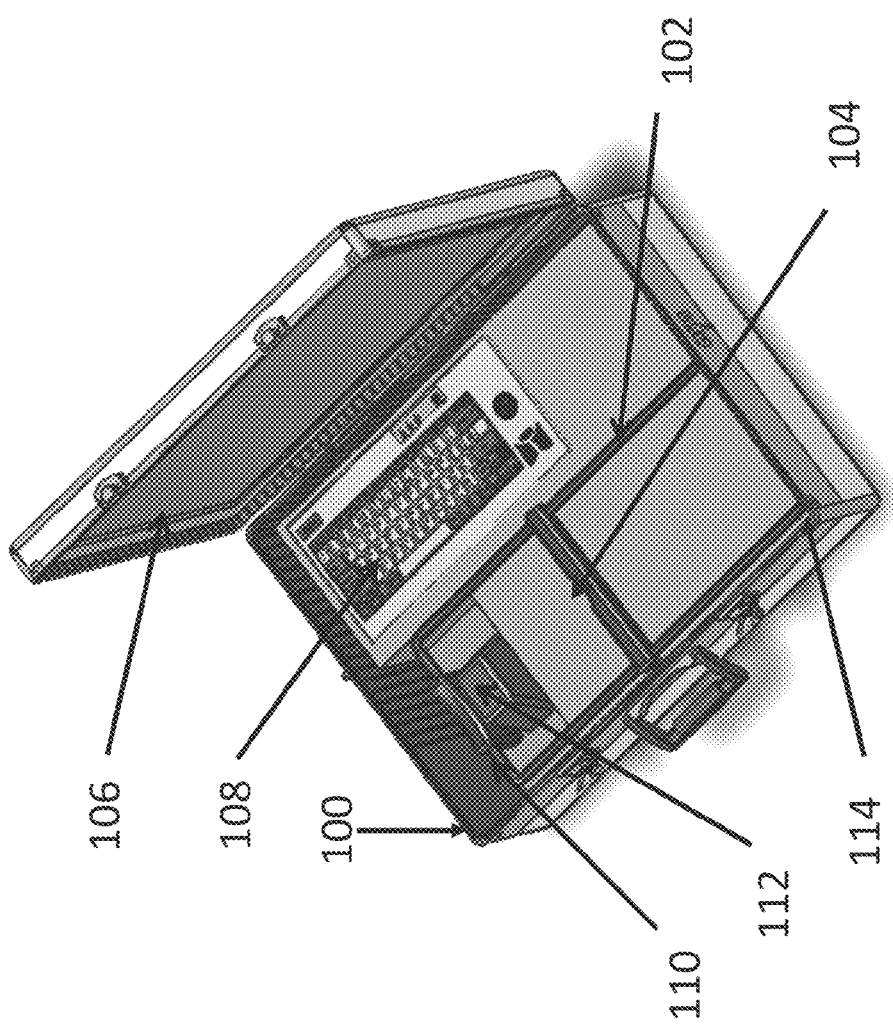
FIG. 2 depicts the folded version of the "foldable face-holder apparatus" 100.

FIG. 2 depicts the folded version of the "foldable face-holder apparatus" 100. It is folded at the hinge 114. In some embodiments, the face-holder can be folded at least once and possibly multiple times. In another embodiment of the instant apparatus, the face-holder can be folded by collapsing multi-stage telescopic legs. In another embodiment, the face-holder comprises of a chin-rest 104 and a forehead rest 110 and only the portion between the chin-rest 104 and the instrument base 118 is collapsible using multi-stage telescopic legs as illustrated in FIG. 3. The collapsed legs are shown as 302 and elongated legs are shown as 304 in FIG. 3.

In one more embodiment, there is a folding hinge 114 at or near the chin-rest 104.

In another embodiment, the proposed ophthalmic system comprises of at least one means to hold the face of a patient (i.e., face-holder) and the means to eject (using a button) or remove the face-holder from the base of the instrument.

In another embodiment, the chin-rest can be removed or ejected from the base of the instrument. In another embodiment, the chin-rest is attached to the base of the instrument. In some other embodiments, the chin-rest-attachment is removable.

In some embodiments, all the apparatus components reside in a brief-case as shown in FIG. 1. In some embodiments, the brief-case has wheels and/or a handle to assist transportation.

In some embodiments, the apparatus operates on batteries. In some other embodiments, these batteries can be rechargeable batteries. The batteries can be charged independently or by connecting a charger to the apparatus. The charger can source power from the electrical wiring in a building. The charger (termed a vehicle charger) can also source power from a vehicle such as a car or a bus or a truck or a van. The charger can also source power from the vehicle's engine.

In some embodiments, the apparatus could comprise of a projector (sometimes termed pico-projector) to display the results on a wall or a screen.

In some embodiments, the apparatus is used for ophthalmic imaging. Ophthalmic imaging includes (but does not limit to) retinal imaging and anterior segment.

In some other embodiments, the apparatus is used for optical coherence tomography (OCT) imaging (as described in Huang et al 1991, Fercher 1996, U.S. Pat. No. 5,321,501). Optical coherence domain reflectometry (OCDR) is a 1-dimensional measurement system as explained in (U.S. Pat. No. 5,202,745), and OCT is a 2-D extension of OCDR (as described in Huang et al 1991, Fercher 1996, U.S. Pat. No. 5,321,501). Since OCT and OCDR are similar, sometimes we would refer these as OCT-OCDR systems. The diagnostic components or systems based on OCT-OCDR, will be called as OCT-OCDR based diagnostic components.

In some other embodiments, the foldable face-holder apparatus comprises for optical coherence tomography (OCT) imaging apparatus and the OCT system apparatus comprises of a spectrometer to implement spectral-domain OCT (as described in De Boer et al 2003, Wojtkowski et al 2004, Hausler & Lindner *J. Biomed. Opt.* 3 (1), 21-31 (Jan. 1, 1998)).

In some other embodiments, the foldable face-holder system is used for optical coherence tomography (OCT) imaging and the OCT system comprises of a tunable wavelength (or frequency) light source to implement swept-source OCT (as described in S R Chinn, E A Swanson, J G Fujimoto—Optics Letters, 1997; M A Choma, M V Sarunic, C Yan et al—Optics Express, 2003; Y Yasuno, V D Madjarova, S Makita, M Akiba et al—Optics Express 2005).

In some other embodiments, the foldable face-holder system is used for optical coherence tomography (OCT) imaging and the OCT system comprises of a depth-scanning reference mirror to implement time-domain OCT (as described in Huang et al 1991, Fercher 1996, U.S. Pat. No. 5,321,501).

In some embodiments, compact, portable OCT-OCDR systems/apparatus (as described in U.S. patent application Ser. Nos. 12/706,717, 12/732,484, 13/723,006, 12/941,991) can be used as these systems/apparatus can easily fit in a box or a briefcase.

Various materials can be used to construct the foldable face-holder apparatus. Some examples are (not by limitation) 6061 aluminum alloy (i.e., UNS A96061) and its various varieties including (but not limited to) 6061-O, 6061-T4, 6061-T4 etc.; Nickel-chromium alloys such as INCONEL® (a registered trademark of the INCO family of companies) alloy 600; stainless steel and related alloys (e.g., UNS N02200, UNS N02201, UNS N04400, UNS N06600, UNS N06625, UNS N08800, UNS N08825, UNS N10276, UNS N08020, etc.) heat and chemical resistant polymers such as TOPAS® COC (by Topas Advanced Polymers). Acetal homopolymer such as Dupont's Delrin® can also be used as these polymers are tough, can sustain high stress and strain and are strong, and yet easily moldable.

Some more materials that can be used to construct the foldable face-holder apparatus include (not by limitation) High-density polyethylene (HDPE), Polyvinyl chloride (PVC), Acrylonitrile butadiene styrene (ABS), Polyether ether ketone (PEEK).

The apparatus can be built (by way of example and not by limitation) by the process of reaction injection molding, which can produce high-strength, lightweight and flexible parts using thermosetting polymers such as polyurethane.

The apparatus could also be built (by way of example and not by limitation) by structural reaction injection molding (SRIM), where fiber meshes are used as a reinforcing agent.

The apparatus could also be built (by way of example and not by limitation) by injection molding, using thermoplastics or thermosetting plastics.

The apparatus could also be built (by way of example and not by limitation) by normal machining and assembly.

In some embodiments, the ophthalmic system comprises of at least one means to hold the face of a patient (i.e., face-holder), an ocular diagnostic or therapeutic component and the means to remove the face-holder 112 from the apparatus and attach to the patient's face. The face-holder's eye-piece 112 is attached to the eyes using a head-band.

In some other embodiments, the face-holder is attached to the eyes using spectacles-type assembly. The eye-piece may be moved from one eye to the other for analyzing both the eyes.

The "foldable face-holder apparatus" and related systems could be used for fundus photography (http://en.wikipedia.org/wiki/Fundus_photography), scanning retinal imaging (e.g., T R Friberg, A Pandya et al 2003), perimetry, corneal topography, auto-refractors, and many other ophthalmic modalities.

What is claimed is:

1. An ophthalmic system comprising of
    at least one means to hold the face of a patient called a face-holder;
    an optical coherence domain reflectometry based diagnostic component to perform diagnosis of the eye;
    a means to fold the face-holder; wherein the face-holder can be folded at least once; and
    the face-holder further comprises of a forehead rest, which is a resting pad to rest the forehead; and
    the face-holder further comprises of a chin-rest, which is a resting pad to rest the chin;
    wherein the face-holder can be folded by collapsing multi-stage telescopic legs, and
    a portion between the chin-rest and the instrument base is collapsible using multi-stage telescopic legs.

2. The system of claim 1, wherein the diagnostic component further comprises of optical coherence tomography.

3. The system of claim 1, where the system fits in at least one of a box and a briefcase.

4. The system of claim 1, where there is a folding hinge near the chin-rest.

5. The system of claim 1, where there is a folding hinge at the chin-rest.

6. The system of claim 1, where there is a folding hinge near the instrument base.

7. The system of claim 1, where there is a folding hinge at the instrument base.

8. An ophthalmic system comprising of
    at least one means to hold the face of a patient called a face-holder and
    a base comprising of electronics and optical components;
    at least one of diagnostic and therapeutic components; and
    a means to remove the face-holder from the base; and
    a means to attach the face-holder to the patient's face; and
    a means for an eye-fixation target; and
    an eye-piece comprising of optics and mechanics used to evaluate the eye; and
    a fiber running from the base to the eye-piece; and
    the eye-piece is able to move from one eye to the other for analyzing both the eyes and
    a screen to display results; and
    the system fits in a briefcase.

9. The system of claim 8, further comprises of the means to eject the face-holder from the base of the instrument.

10. The system of claim 8, wherein the system comprises of ophthalmic imaging.

11. An ophthalmic apparatus comprising of
    at least one means to hold the face of a patient called a face-holder;
    at least one diagnostic component to perform diagnosis of the eye;
    a foldable face-holder wherein the face-holder can be folded at least once; and
    a means for an eye-fixation target; and a screen to display measurement results; and an eye-piece which is an optics and mechanics used to evaluate the eye; and a base comprising of electronics and optical components; and cables running from the base to the eye-piece.

12. The apparatus of claim 11 wherein the display screen is a touch-sensitive screen.

13. The apparatus of claim 11 wherein the apparatus operates on batteries.

14. The apparatus of claim 11 wherein the apparatus operates on rechargeable batteries.

15. The apparatus of claim 11 further comprising of a vehicle charger to charge the batteries by sourcing power from a vehicle.

16. The apparatus of claim 11 further comprises of optical coherence tomography imaging.

17. The apparatus of claim 11 where the diagnostic component comprises of ophthalmic imaging.

18. The apparatus of claim 11 where the apparatus further comprises of a spectrometer.

19. The apparatus of claim 11, wherein the diagnostic component is based on optical coherence domain reflectometry.

20. The apparatus of claim 11, where the apparatus is built by the process of reaction injection molding.

* * * * *